United States Patent [19]

Bremer et al.

[11] Patent Number: 4,526,176
[45] Date of Patent: Jul. 2, 1985

[54] LONG-LIFE BIOMEDICAL APPLICATION DEVICE, PARTICULARLY ELECTRODE, AND METHOD OF TRANSFERRING ELECTRICAL CURRENT

[75] Inventors: Roger E. Bremer, Fort Lee; Charles Anthony, Jr., Livingston; Raymond M. Chappel, Mendham, all of N.J.

[73] Assignee: Frantz Medical Development Ltd., New York, N.Y.

[21] Appl. No.: 333,287

[22] Filed: Dec. 22, 1981

[51] Int. Cl.³ .............................................. A61B 5/04
[52] U.S. Cl. .................................... 128/641; 128/803
[58] Field of Search .............................. 128/639–641, 128/644, 798, 802, 803, 403; 604/20, 306

[56] References Cited

U.S. PATENT DOCUMENTS

| | | | |
|---|---|---|---|
| 3,187,745 | 6/1965 | Baum et al. | 128/639 |
| 3,340,868 | 9/1967 | Darling | 128/640 |
| 3,580,254 | 5/1971 | Stuart | 604/306 X |
| 3,702,613 | 11/1972 | Panico et al. | 128/803 |
| 3,763,622 | 10/1973 | Stanley, Jr. | 128/403 X |
| 4,079,731 | 3/1978 | Danby | 128/641 |
| 4,117,841 | 10/1978 | Perrotta et al. | 604/306 X |
| 4,215,696 | 8/1980 | Bremer et al. | 128/641 |
| 4,270,544 | 6/1981 | Gilden et al. | 128/641 |

FOREIGN PATENT DOCUMENTS 724144  3/1980  U.S.S.R. .............................. 128/803

Primary Examiner—Lee S. Cohen
Attorney, Agent, or Firm—Frishauf, Holtz, Goodman & Woodward

[57] ABSTRACT

To separate electrolyte (70) within a chamber (66) formed beneath a dome-like housing (24) from a signal transmission connector (34) and thus prevent corrosion of the terminal portion (38, 40) exposed to the interior of the chamber by the electrolyte, the interior of the chamber (66) is subdivided into two chambers (166, 266) by enclosing within said chamber a plastic bag (101) or stretching a membrane (102) thereacross, the subdividing means (101, 102) being ruptured upon depression of the contact terminal (34) of the housing; the electrolyte is retained solely within the chamber (266, 266a) separate from the interior portion (38, 40) of the terminal so that the corrosive influence of the electrolyte is prevented from attacking the metal of the terminal prior to use of the electrode, and during storage. Preferably, the chamber (166, 166a) to which also the terminal is exposed may retain other liquids which are inert with respect to the electrode, and which, preferably, are also separated from the electrolyte, such as a surfactant (170) to, additionally, permit a wider choice of, respectively, electrolytes and surfactants without unintended leakage of electrolyte through the microporous membrane (76)closing off the housing.

19 Claims, 6 Drawing Figures

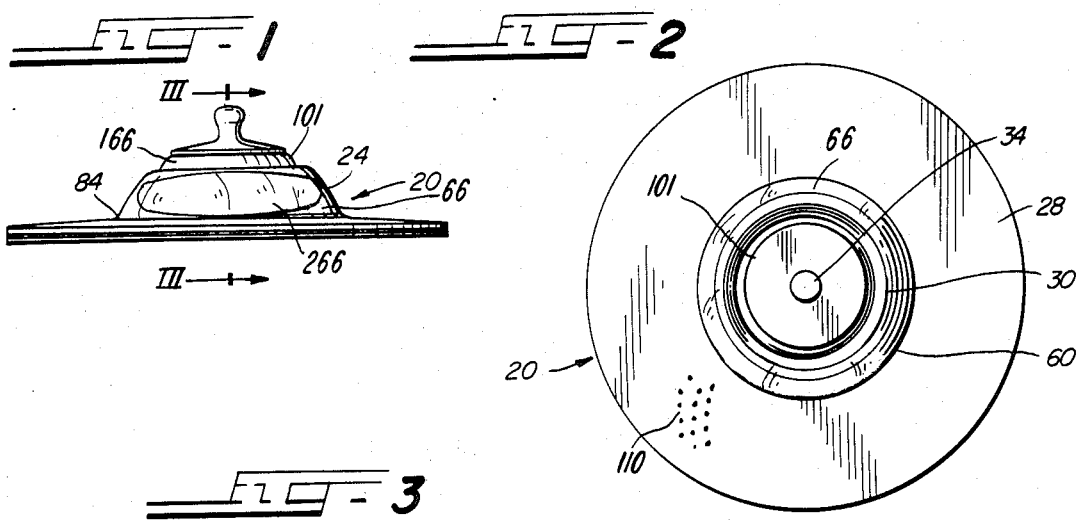
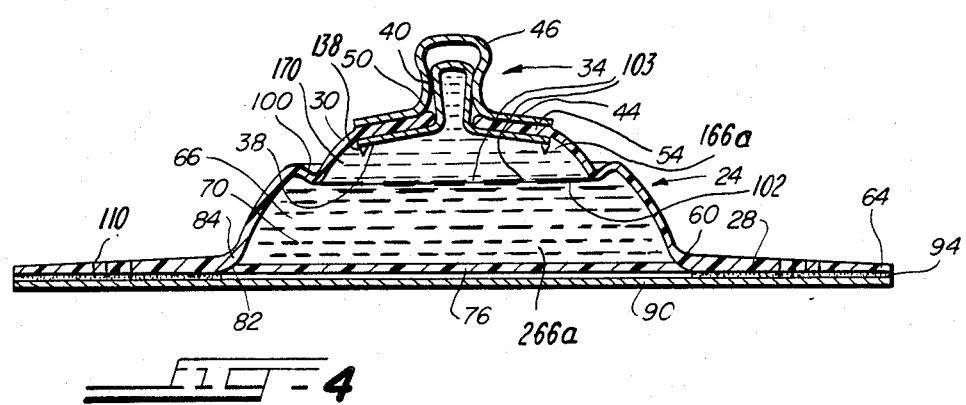
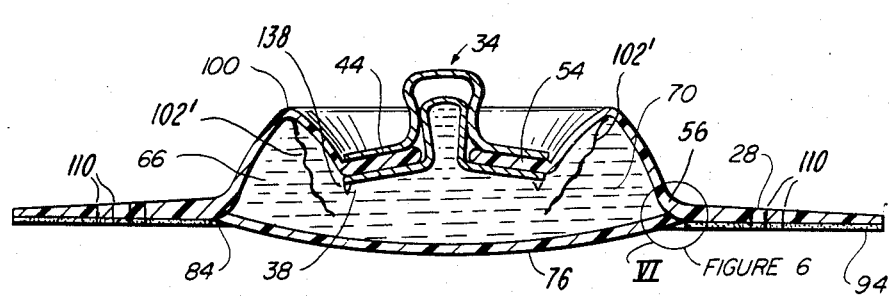
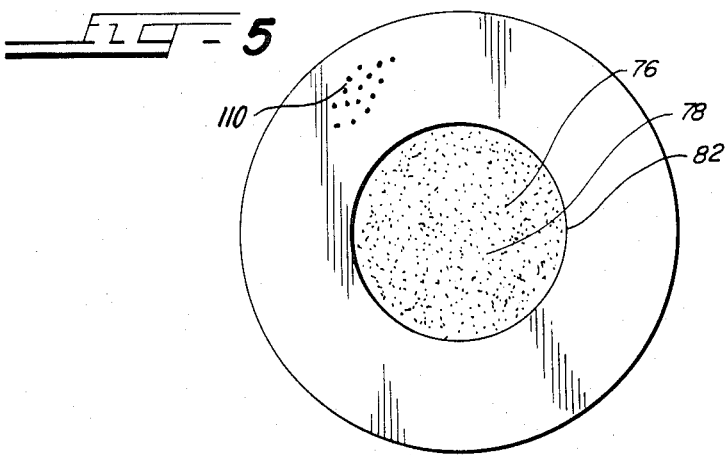
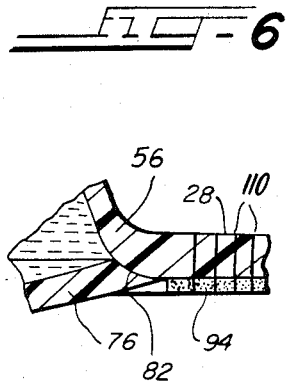

LONG-LIFE BIOMEDICAL APPLICATION DEVICE, PARTICULARLY ELECTRODE, AND METHOD OF TRANSFERRING ELECTRICAL CURRENT

Reference to related U.S. Pat. No. 4,215,696, Bremer and Falb.

The present invention relates to a biomedical electrode which can be applied to the skin of a patient to provide electrical contact to the skin, and more particularly to such an electrode in which the contact resistance with the skin is low and unvarying over a long period of time, as well as uniformly persistent during use.

BACKGROUND

Various types of biomedical electrodes to transfer current signals between an external circuit and the skin of a person have been proposed. In order to provide good electrical contact between an electrical terminal, typically a metal element, and the skin of the person, it is customary to apply an electrolyte between the connecting points of the electrode and the skin. This electrolyte may be in the form of a gel. It can be applied directly from a gel tube or, in another form, an electrode element having a fixed electrical contact which, in turn, is an electrical connecting contact with the gel is applied to the person. The electrolyte can be absorbed, for example, in a sponge which is in contact with the contact button, or can be located in a chamber closed off by a microporous membrane so that the electrolyte, then typically a liquid, can be forced through the pores or openings closing off the chamber, for example ooze through the membrane upon application of pressure thereto.

U.S. Pat. No. 4,215,696, Bremer and Falb, describes a biomedical electrode for pressurized skin contact, and uses and applications thereof, which is disposable and includes a vaulted dome-like electrolyte-containing chamber or cavity which is bridged at its open bottom by a highly flexible, conformable and hydrophobic microporous membrane. For storage, the membrane is covered with an adhesively secured protective film which is adapted to be stripped preparatory to adhesively securing the electrode to the skin of a patient. The electrode material and shape are such that the vaulted housing can be physically distorted upon downward pressure applied thereto to force electrolyte within the chamber to diffuse through the conditioned microporous membrane into positive and low-electrical resistance contact with the skin surface of the patient. The housing maintains a positive, resilient sustained pressure of electrolyte against the skin surface due to the change in configurations of the internal volume of the chamber which contains the electrolyte upon deformation thereof, thus contributing to low-impedance electrical continuity between the skin of the patient or subject and an electrode terminal. Disruptive variations, which are objectionable in many types of electrodes applied to patients and result in change in signal strength, are minimized. Instantaneous electrical response and rapid stabilization are enhanced by the electrode in which electrolyte fluid is maintained in a continuous path through the microporous membrane against the skin.

The electrode described in the aforementioned patent has the additional feature of a ring-like transformation zone which circumscribes the housing at a height intermediate the upper and lower limits thereof, to form a mechanical discontinuity and, in essence, a snap-over or toggle action upon deformation of the housing. The zone, additionally, provides for two stable positions of the housing; one in which the housing is essentially dome-like, and another in which the housing is in compressed condition, in which fluid pressure assists electrolyte flow through the microporous membrane. This second position provides for a stable orientation of the housing with respect to the microporous membrane and establishes a constant pressure of the electrolyte against the membrane to provide a continuous conductive path between the body surface of the subject and a terminal of the electrode in contact therewith.

THE INVENTION

It is an object to improve an electrode to be applied to the skin of the user by providing an element which has an enhanced shelf life, better electrical contact than heretofor obtainable, and which permits a wider selection of materials for use within the electrode, for example as electrolyte, or as additives enhancing the electrical current transfer characteristics of the electrode element.

Briefly, in accordance with this invention, the electrolyte is confined within the chamber to be out-of-contact or communication with an electrode contact button having a metal portion therein, so that the electrolyte—which typically includes a sodium chloride solution or similar salt solutions,—cannot corrode or otherwise attack the metal or conductive metal salts which form the electrical contact of the electrode.

In accordance with a feature of the invention, the electrolyte is retained within a separate subchamber or container which, upon deformation of the housing, is ruptured to permit electrode button contact with the electrolyte within the main chamber. In accordance with an embodiment of the invention, the chamber is subdivided by a thin rupturable or frangible membrane, for example made of a polypropylene base material which may be formed with weakened, rupturing portions. The membrane can be attached to the housing, for example at a zone of transition or transformation which can cause toggle or snap-over action thereof. The electrolyte is retained in the main chamber below the membrane, separate from the electrical contact button. The space between the membrane and the electrical terminal may be used to include a fluid or gel therein which does not attack the electrode, and may include a surfactant e.g. of non-ionic or ionic type, or may contain additional substances e.g. which improve the stability of electrical contact.

In accordance with another embodiment of the invention, the housing defines a chamber therein which is closed off at one side by a microporous or similar porous membrane. The chamber is subdivided internally by enclosing the electrolyte and/or other substances in one or more small bags, for example of plastic, and other material which can be ruptured upon deformation of the housing, for example by squeezing it. The electrolyte, being retained in a separate bag within the housing chamber thus is separated from the electrode terminal before rupture. The space between the bag enclosing the electrolyte and the remainder of the housing can be taken up to a fill including, for example, a surfactant or additional substances to improve the stability of electrical contact. More than one such bag may be located within the chamber defined by the housing.

The electrode described in the aforementioned Patent 4,215,696 functions reliably and well; the electrode in accordance with the present invention is an improvement thereover and substantially extends the shelf life of the prior electrode, and increases the current typically ionic current carrying capacity thereof, so that the electrode is more flexible and adaptable to multiple applications, in addition to monitoring and stress-testing such as defibrillation, neonatal use, or for testing or other uses, for example, in an electrocardiogram apparatus, EEG's, biofeedback and Trancutaneous Electrical Neuro Stimulator (TENS), with minimum changes.

Thus, stocking problems and shelf life problems are reduced since the electrolyte and the contact materials are clearly separated before use, and brought into contact only upon application to the skin of a user, so that the output signals which are passed through the electrode will not be affected by prior conditions and parameters, such as shelf time, heat, and the like, over which the doctor or other medical person using the electrode, has no control. The signals being applied to the electrode will be reliably transferred by the electrode, unaffected by the electrode element itself, i.e. during the period of application on a person in the monitoring, stress-testing, clinical ECG, or pacing diagnostic modes, or for defibrillation.

The electrode is suitable for clinical diagnostic electrocardiograms (ECG's) as a result of its intrinsically low manufacturing cost, and the linear signal transfer performance characteristics, and its ability to have long shelf life, coupled with uniformity of performance, high quality and signal pick-up and fidelity. It eliminates the use of separately applied gels, and reduces skin preparation requirements.

The electrode provides the following advantages compared to the currently available disposable pregelled sponge ECG electrodes:

(a) Shelf life characteristics: In current models of electrodes, the metal (silver/silver chloride) electrode contact button is susceptible as a result of its contact, during the life of the unit to deterioration with the salt-based electrolyte gel impregnated in a sponge therein. The unit of the invention provides for contact between the fastener and the electrolyte only at the time the electrode is applied to the body, thus, reducing the time for deteriorating interaction between the salt-based electrolyte and the silver/silver chloride to a maximum of seven days as compared with many months. This inherent design safeguard is particularly important because it is not possible to measure the extent to which any single electrode has been subjected to this deterioration process and still retain the integrity of the electrode such that it may remain functional. Sampling techniques are only inferential because of the variability inherent in manufacturing techniques and storage conditions.

(b) Separation of components in the electrode: Various additives are separated from either the electrolyte or the fastener until the electrode is ready for application. It is necessary to insolate these additives which may include: surfactants, moisture retaining substances, (humectants), skin penetrants and silver chloride due to the nature of the additives and their purposes. For example, the surfactant improves the permeability of the electrolyte; this action is desirable, however, only upon application of the electrode to the body. Prior to application, it may cause leakage of electrolyte. Silver chloride within the electrolyte chamber reduces the complexing of the silver chloride on the contact button during the useful life of the electrode. The electrode isolates the substances in the chamber until the electrode is activated for use. The performance permits selection of more effective and heretofore unusable materials due to incompatibility thereof if in extended time contact.

(c) A single integrated electrode system is provided:
External gels, etc., are not needed, as the electrode contains a liquid electrolyte, which is a medium for conducting physiological signals or better quality, subject to less impedance, superior to gels.

Various parameters are effectively balanced; surfactants, humectants, liquid viscosity, membrane surface tension and mechanical pressure in order to introduce the electrolyte into the skin pores, dissolve sebum, help overcome the resistance of the stratum-corneum, and induce other electro-chemical actions to assure a surerior signal, and reduces or eliminates the need for skin abrasion.

Shelf life: by separating the silver/silver chloride fastener from the electrolyte during the storage period shelf life is substantially extened.

Interference rejection: Continued superior performance is assured even after a series of high voltage interferences caused by defibrillations.

Range of applications: Monitoring and stress-testing, besides ECG and other applications, thus, reducing the need for multiple model stocking and the resulting higher inventory cost and possibility for confusion in use.

Other uses: The separation of various materials into a multi-chamber unit allows for the application of this system to:EEGs, other neurological and physiological signals, and transcutaneous drug application.

Inspection: Visual check of the electrolyte is possible by making the housing transparent, and permits color-coding of the electrolyte.

Drying out: Dry-out during actual use is reduced.

Application: Use of gels applied externally at individual locations is eliminated. Gels are messy to use and may come into contact with the adhesive, particularly during emergency applications, thus reducing the adhesion of the electrode to the body and permitting motion or detachment. Likewise, impregnated sponges which are subject to non-uniform concentrations of gel within the sponge mass are eliminated.

Sterility: A more sterile, less irritating surface contact with the skin is obtained through the use of: a membrane which is impervious to bacteria migration; a flange material which allows for air to pass through to the skin surface; and the reduced need for skin abrasion prior to electrode application.

Cost: Manufacturing costs are low due to the intrinsically simple design and inexpensive production materials. The electrode thus is economical for single use, e.g. for clinical diagnostic ECG's.

DRAWINGS

FIG. 1 is a general pictorial representation of the device in form of an electrode is essentially phantom side view, in which the electrode housing can be considered to be transparent;

FIG. 2 is a top view of the electrode of FIG. 1;

FIG. 3 is an enlarged cross-sectional view taken substantially along lines III—III of FIG. 1, and illustrating the electrode of the invention prior to its attachment to a body surface, for example the skin of a patient;

FIG. 4 is a cross-sectional view similar to that illustrated in FIG. 3, and showing the configuration of the electrode after the housing has been forcibly deformed by being pushed downwardly to establish pressure on the electrolyte with and against the body surface of the patient, to which the electrode is secured;

FIG. 5 is a bottom plan view of the electrode; and

FIG. 6 is an enlarged fragmentary view of the zone identified by the circle VI in FIG. 4 and showing, a schematically, the configuration of the juncture of the electrode housing with the microporous membrane which bridges the opening at the base of the housing.

The drawings, FIGS. 1–6, conform essentially to the drawings of the aforementioned referenced U.S. Pat. No. 4,215,696, and the same reference numerals used therein are also being used herein.

DETAILED DESCRIPTION

The invention will be described in connection with an electrode. The electrode 20, generally, has an inverted essentially dish-shaped plastic housing 24 bounded by an annularly, laterally extending flange or rim 28. Housing 24 has a vaulted, dome-like roof 30. A terminal 34 is sealed to the roof 30 at the apex or center thereof. Terminal 34 extends through the roof 30 and provides an electrically conductive path between the exterior of the housing 24 and its interior. The terminal 34, for example, is a two-part button structure of well known and standard configuration.

Terminal 34—see FIG. 3—is a male snap-fastener assembly consisting of a first, inner washer-like disk 38 and a central integrally formed upwardly extending stud 40 element, and a second outer snap, fastener element formed by a conductive cap 44 and having an upwardly projecting, downwardly open outer stud to receive inner stud 40.

Terminal 34 is secured to the roof 30 of the housing 24. For assembly, the stud 40 of the lower component 38 is inserted upwardly to extend through the opening 50 at the apex of the roof 30 of the housing into the cooperating socket 46 of the cap 44. Parts 38, 44 are then forcibly pressed or crimped together to establish a mechanical interlock and to form a fluid-tight joint with the interposed plastic housing 24.

The effectiveness of the seal between the roof 30 and the housing 24 and terminal 34 is insured by forming the upper extremity of the plastic housing with an integral, somewhat thickened ring-like annular bead 54. Bead 54 is pinched on its upper and lower surfaces by the annular flanges of disk and cap 38, 44, and defines a mechanically strenghtened, compressible zone.

The integral annular flange 28 at the base 56 of the housing—see FIG. 3—is formed with a transverse thickness gradient which tapers from a greater thickness at its inner radial origin 60 adjacent its juncture with the vaulted housing wall to a lesser thickness at its outer marginal end 64—FIG. 3—to provide physical strength, rigidity and stability in conjunction with enhanced conformability of the flange 28 to a body surface (not shown) of the patient, to which the flange 28 is to be ultimately adhesively secured.

The open face of the electrode housing 24 is bridged by a microporous membrane 76. The openings 78 are exceedingly small, but large enough to permit fluid passage therethrough. An example of a suitable plastic membrane is sold by Celanese Plastics Company under the trademark "CELGARD" Type 2400, or K-456. The membrane 76 itself may be secured to the housing 24 in various ways. In a preferred embodiment, the membrane 76 is bonded ultrasonically to provide a ring seal 82—see FIG. 6—at the juncture 84 of the housing wall with the horizontally extending flange 28. The junction of the flange 28 with housing 24 is microconvoluted or knurled, a configuration which facilitates ultrasonic bonding of the membrane 76 to flange 28 and to insure a positive, fluid-tight seal.

To prevent escape of fluid from the chamber defined beneath the housing 24 through the membrane 76 prior to use, a peelable, non-permeable strip sheet or film 90 is provided which covers and temporarily seals the membrane 76. The cover film is secured to the lower surface of the surrounding annular flange 28 by an interposed pressure-sensitive adhesive 94. The same adhesive which is exposed upon stripping of the protective film 90 also is used to anchor the electrode assembly 20 firmly in place on the skin surface of the patient or subject. The adhesive used can be of the liquid compatible, emulsified type because the electrolyte 70 can be liquid, as contrasted with a gel.

The configuration of the chamber or cavity 66 beneath the housing 24 and above the membrane 76 can be changed, the configuration being capable of assuming two stable states. Reference is made both to FIGS. 3 and 4, which show the unit in two different positions. As assembled, and prior to actual use of the electrode, the housing 24 is vaulted upwardly—see FIG. 3. The housing wall is formed with an offset band or inflection at its circumference to provide a ring-like transformation zone 100 which extends annularly about the housing. The zone generally parallels a plane defined by the microporous membrane 76. This transformation zone 100 functions as a mechanical discontinuity or toggle joint condition in the housing wall.

An alternate configuration is to replace the continuous flange 28 with a separate flange made of either a woven, nonwoven or film material of the same horizontal dimensions and simultaneously bonding same to the dome portion of the electrode at joint 84, in a ring seal 82, when membrane 76 is bonded to housing 56 a junction seal 82, per FIG. 6; or to continue membrane 76 beyond juncture at 56 and use as the flange. A speckled application of the adhesive and permeability of the membrane permit the skin to breath.

USE AND OPERATION

With the electrode adhesively secured in place on the skin surface of a subject, application of downward pressure, for example finger pressure to the vaulted roof of the housing at the center terminal 34 causes the dome-like roof of the housing to be displaced downwardly and snap into the stable position shown in FIG. 4. The flexing zone 100 is then located at the upper edge of the now toroidal housing. This action initially distends the microporous membrane by an amount equal to twice the volume of the upper dome. The distended membrane with its resiliency maintains continuous pressure on the electrolyte providing a pressure driving force which assists electrolyte flow through its pores. The mechanical shift of the housing wall is somewhat analogous to a toggle phenomenon, since the depressed position of the roof of the housing constitutes a new stable orientation, and pressure within the cavity is maintained as a continuing state.

A suitable electrolyte 70 for biomedical use is a salt solution, such as sodium chloride, in an aqueous solution. Various types of electrolytes may be used; the referenced U.S. Pat. No. 4,215,696 contains a discussion of suitable materials.

In accordance with the present invention, signal variations under otherwise identical conditions from different electrodes can be effectively controlled, and the storage life of the electrode unit themselves substantially increased—theoretically practically indefinitely—by separating the electrolyte from the metal of the contact terminal. The present invention is, in part, grounded on the realization that difficulties with use of such electrodes are often associated with the corrosive effect of the electrolyte on the metal of the contact button, and specifically on the flange 38. Accordingly, and in order to avoid such difficulties, the contact botton and the electrolyte are separated from each other. Referring to FIG. 1: A small plastic bag 101 for example in form of a small capsule, is placed into the cavity 66 before application of the membrane 76. The plastic bag 101 has a frangible, or easily breakable skin. The cavity 66, thus, is subdivided into two portions 166, 266, portion 166 being outside the bag 101, and portion 266 within bag 101. The cavity 166 can retain a fluid which is inert with respect to the metal used for the contact or terminal 34; it may, for example, contain a nonionic or an ionic surfactant. Separating the cavity 66 into two independent portions 166 and 266, of which one portion 266 retains the electrolyte 70 and the other is in contact with the metal electrode, substantially increases the scope of possible materials which can be used with the electrode and thus further improves its operating performance. The potential vagaries of reactions of multiple chemicals in solution over extended shelf life can thus be considered. The isolation of the metal of the connector 38, FIG. 3, from the metal/salt electrolyte solution provides greater range of choices for the metal of the connector, and of the electrolyte composition, an important consideration for blending economy and disposability.

The viscosity of the electrolyte material within the chamber 266 can be higher than that of the prior art electrode of U.S. Pat. No. 4,215,696, and diffusion of the electrolyte through the membrane 76 and the microporous openings 78 therethrough more easily controlled than heretofore possible, since some leakage through the membrane, even with the strip 90 applied, is effectively prevented. Before rupturing of the plastic bag 101, the surfactant or wetting agent which contributes to passage of the electrolyte through the microporous openings 78 of the membrane 76 is separated therefrom. Further, by control of surface tension and viscosity, better penetration of electrolyte through the membrane 76, when desired, can be effected by addition of and under control of the surfactant. The surfactant is inert with respect to the plastic or metal material of the housing and contact terminal 34 and the plastic material of the bag 101. Separating the surfactant and the electrolyte also results in better temperature stability and, of course, consequent additional increase in shelf life and reliability of operation under varying storage conditions.

Users of present pre-gelled electrodes with their gel in contact with their silver-chlorided connectors have no way of confirming their degradation, meta complexing or electro-chemical interaction over long periods of shelf life; or the consequences of these conditions aggravated by a series of high voltage exposures during a series of defibrillations while the electrode is applied to the patient. Testing them before application does not confirm performance on the patient; once used they cannot be accurately tested. The separation, as described, provides prima facie assurance against these reactions, since an effective isolation is evident.

The choice of the surfactant and the balance thereof with and tolerances than if surfactant and electrolyte are initially mixed and remain mixed prior to use and during use. Initial separation of the ingredients of the combined fluid within the chamber 66, when the plastic bag 101 has been ruptured upon depression of the contact button—see FIG. 4—thus provides advantages beyond those arising from separation of the components alone.

Various types of contact buttons contain silver chloride, for example in the form of coatings. Silver chloride and sodium chloride in the electrolyte interact, and the sodium chloride tends to corrode or form a complex with the metal of the contact button 34. It is possible, however to add a measured amount of silver chloride which saturates the electrolyte 70 within the chamber 266. After rupturing of the plastic bag 101, the time that the sodium chloride will be in contact with the metal of the button, that is, during use, which may extend to a maximum of seven days in a monitoring application—for instance to make repetitive measurements—will not be sufficiently long to cause corrosive interaction, or to degrade the various components then within or in contact with the mixture in the cavity 66, because the salt solution in which silver chloride has been saturated will not be disposed to leach more silver chloride from the surface 38, nor to complex therewith; and serious chemical interactions will not occur in this short period.

To facilitate rupture and insure breakage of the bag 101 upon deformation of the housing 24, the inner flange 38 may be formed with downwardly extending tips, points, or burrs 138 (FIGS. 3,4) to provide for penetrating break points to readily pierce the frangible bag 101.

In accordance with another embodiment of the invention, see FIGS. 3 and 4, the chambers 166, 266 are formed by introducing a separating membrane 102 between the upper portion of the housing and the lower portion to thereby separate the cavity 66 into two portions 166a, 266a. Chamber 166a thus can retain the non ionic or ionic surfactant or any other substance described in connection with chamber 166, FIG. 1. The separation membrane 102, preferably, is made of a polypropylene base with additives, such as glass fibers, mica, talc or mineral fillers or other materials, which can be sealed to the main housing 24, to the rupturable or friable upon deformation of the housing 24 from the position shown in FIG. 3 to the position shown in FIG. 4. The ruptured ends of the membrane are shown at 102' in FIG. 4. Use of the membrane has the advantage—for example with respect to FIG. 1—of ease of manufacture. Preferably, the membrane 102 is connected to the housing 24 by a welding technique. Ultrasonic bonding of the membrane permits ready control of the bonding process and is ideally suited to the three polypropylene elements to be welded. The bottom membrane 76 also is, preferably, welded to the housing, e.g. by ultrasonics. An ultrasonic bonding process is preferred since it is simple, reliable and adaptable for use with very thin frangible membranes and/or membranes of the microporous type.

When using the embodiment of FIG. 3, the upper chamber 166a preferably contains the surfactant which will not affect a metal contact button with a silver chloride coating. The upper chamber may also contain other additives, such as, for example, DMSO (dimethyl-sulfoxide), a skin penetrant; a sweat inducer and anti-bacterial agents such as parabens.

It is also possible to combine additives with the electrolyte 70 in chamber 266a, depending upon chemical preferences and compatibility. Enzymes may also be added to the electrolyte and/or within the upper chamber, to obtain better skin contact by penetrating the stratum corneum (dead skin layer) and helping the contact transfer of electrical signals between the electrode contact button 34 and the subject or patient, and reduces or eliminates the need for skin abrasion.

Separating the electrolyte 70 in chamber 266a from the fill in chamber 166a, which can include selected components desirable for good signal transfer, thus permits extended shelf life while providing electrodes with more consistently uniform characteristics; additionally, the electrolyte can be so selected that its current carrying capability is increased over that heretofore possible in view of the prior limitations due to the corrosive nature of the electrolyte 70. The electrodes thus, are more suitably interchangeable for defibrillation as well as for diagnostic and signal transfer applications for various types of patients.

The extending flange or rim 28 of the housing 24, which is made of plastic, preferably is perforated as seen at 110 to provide skin breathing holes, similar to perforations in plastic adhesive strips of small, self-holding bandages. This inhibits anaerobic bacterial build-up and together with included anti-bacterial material, such as parabens provides a more sterile environment.

The membrane 76 is hydrophobic. By control of surface tension and viscosity of the electrolyte to pass therethrough, the electrolyte can penetrate through the membrane. Adding a surfactant to the electrolyte permits a balance of forces inducing proper penentration and facilitates the passage. Separating the surfactant, prior to the time when the electrolyte 70 is to be released through the membrane, by separating the cavity 66 into the two portions 166, 266; or 166a, 266a, prevents premature seepage through the microporous membrane 76 by the electrolyte 70.

To assist breakage, the membrane 102 is preferably scored or grooved to form break or score lines 103 (FIG. 3); and has an additive(s) therein, such as glass fibers, mica, talc, mineral fillers or other materials to assure absolute rupturability.

Separating the electrolyte from the electrode permits the use of chemically balanced surfactants of such formulation that, when included in the electrolyte formulation, the perfusion of the electrolyte under pressure of the snap-down is assisted. Thus, considering the balance with the pressure, sufficient electrolyte flow on and into the skin pores and hair follicles is metered to chemically penetrate the sebum; the signal conducting resistance of the stratum corneum (inert dead-skin insulation layer)—a difficulty with the gel electrolytes is reduced. Suitable surfactants such as sodium dioctyl sulfosuccinate have been found which used with sodium chloride electrolytes will provide a surface tension reduction sufficient to provide the proper wetting of the membrane material.

Separation also permits introduction, upon mixing during use, of substances in the electrolyte formula, which can be chosen to control the flow rate of the electrolyte through the membrane or humectants to control evaporation losses while electrode is in use; or agents to reduce the galvanic skin response. The electrolyte so composed tends to balance with skin moisture conditions to assist in more uniform ion conduction under variable ambients of heat, humidity, and skin conditions.

The electrolyte 70 is exposed to the metal of the terminal 34 only after or just before being placed on the patient. Thus, electrolyte formulation need only assure against the chemical reactions with the connector 34 for a maximum of about 7 days—the maximum anticipated period of the electrode on the patient. Shelf life is not a factor, as in prior art electrodes, where the gel or other electrolyte 70 and connector 34 are in contact, or not fully isolated when not in use. The present structure permits use of multiple valence salts such as magnesium chloride providing higher ionic conductivity. Other chemical compounds might also be used, and because of this flexibility other metals or metal plating components than silver/silver chloride can be used providing manufacturing economics. Skin compatibility of course is essential.

The combination of separation of electrolytes from the terminal with the snap-down housing feature provides the solution to the separation of the electrolyte from the connector material while in storage and until put into use on the patient. A scored membrane 102 or plastic film with a diameter slightly larger than the connector, over the connector 34, with the film resting on, and heat-sealed or preferably ultrasonically bonded to the housing, adds very little cost. The material cost is insignificant; the operation can be done after crimping of connector 34 without inherent delay in the processing cycle. Once in place, the electrode is isolated from the connector, thus assuring long undegraded shelf life unchallenged by metal interactions. Upon application to the patient and snap-down of the housing, the membrane or film 102 ruptures, thus exposing the electrolyte 70 to the connector 34.

After rupture of membrane 102, and once the electrode is in the operating mode, the chemical balance of the electrolyte can readily be devised, by the right saturation level of silver chloride in the electrolyte, to discourage attack on the silver chloride of the contact button 34. This assures optimum, uniform and consistent performance for the short periods of contact of terminal 34 and electrolyte 70 required for application and use of the terminal.

More than one bag 101, or membrane 102 may be placed in the chamber 66 defined by the housing, to separate different substances. Further, a combination of separating means may be used, for example a bag 101 with a substance included therein can be placed in the chamber 166a or 266a (FIGS. 3,4) with a third substance within that bag, separated from the substance, or substances in the respective chamber. If two or more bags 101 are used, then the chamber 66 beneath the housing can be left empty, i.e. contain air, or even be evacuated.

The housing structure need not be designed to have a snap-over or toggle action although, in a preferred form, the housing can be so made. It is sufficient if the housing is of a material which can be deformed, for example by squeezing it, while maintaining its structural integrity to prevent the escape of the contents thereof while, yet, permitting application of sufficient force to break the respective separating element, for example the membrane 102, or the bag 101.

Various changes and modifications may be made, and features described in connection with any one of the illustrations may be used with any of the others, within the scope of the inventive concept. For example, the membrane 76 can be extended to also form the flange 28; or a separate flange element, e.g. in ring or strip form can be received to the housing at the joint 82 (FIG. 6) as devised.

We claim:

1. Long storage life multiple purpose biomedical electrode
   for use on a subject for transferring electrical current between an external circuit and a body surface of the subject having
   a generally inverted dish or cup-shaped housing (24) of a deformable material, and defining a chamber (66) therein, said housing including a roof (30), and a base (56) and being formed with an opening at the base:
   a hydrophobic microporous, inducible fluid-permeable membrane (76) secured to said housing at the base, said membrane covering the opening in said housing and closing the chamber (66);
   a peelable, releasable fluid-impervious protective cover film (90) overlying said membrane;
   a liquid-compatible, pressure-sensitive adhesive means (94) securing said releasable cover film (90) to said base (56),
   said protective film being selectively removable to expose said membrane and permit attachment of said electrode to a body surface;
   electrically conductive terminal means (34) sealed to and extending through said roof of said housing and providing electrically conductive communication between the exterior of said housing of said electrode and said chamber (66);
   and comprising, in accordance with the invention,
   means (101, 102) for subdividing said chamber into a first chamber portion (166, 166a) and a second chamber portion (266, 266a),
   the terminal means (34) having an exposed electrically conductive portion (38, 40) in said first chamber portion (166, 166a),
   said subdividing means (101, 102) being of frangible material subject to rupture upon deformation and displacement of a wall of the housing;
   tissue-compatible electrolyte means (70) for conducting electrical current, substantially filling said second chamber portion (266, 266a), said electrolyte means being separated from said exposed electrically conductive portion (38, 40) of the terminal means (34) prior to rupture of the subdividing means, and
   wherein the first chamber portion (166, 166a) retains therein at least one material selected from the group consisting of a surfactant, a skin penetrant, a sweat-inducing agent, and an antibacterial agent.

2. Electrode according to claim 1, wherein the first chamber portion (166, 166a) retains therein a surfactant to reduce surface tension at an interface of said electrolyte means (70) and said microporous membrane (76), said surfactant and said electrolyte means mixing upon rupture of said subdividing means to facilitate passage of said electrolyte means (70) through said microporous membrane at the viscosity of the electrolyte means (70) and enhancing effective wetting of the body surface at the zone of securement of said electrode thereto after deformation of the housing (24) and upon use of the electrode upon application to a subject.

3. Electrode according to claim 1, wherein said subdividing means comprises a separate frangible plastic bag (101) located within the chamber (66) and subdividing said chamber into said two chamber portions (166, 266), the volume within said bag (101) forming said second chamber portion (266).

4. Electrode according to claim 1, wherein said subdividing means comprises a frangible separating membrane (102), impervious to the electrolyte means in the second chamber portion (266a) and subdividing said chamber (66) into said two chamber portions (166a, 266a).

5. Electrode according to claim 1, wherein the housing has a dome-shaped roof;
   the subdividing means comprises a frangible separating membrane extending across the housing;
   and a ring-like transformation zone (100) is provided, circumscribing said housing at a height intermediate upper and lower limits thereof, said transformation zone extending in a plane generally parallel to said fluid-permeable membrane (76) and forming a mechanical discontinuity of the wall of said housing, said dome-shaped roof of said housing being displaceable downwardly in response to pressure applied thereto to deform said housing at said transformation zone.

6. Electrode according to claim 5, further including an ultrasonically produced ring seal (82) securing said microporous membrane (76) to the housing (24);
   and an ultrasonically produced attachment weld securing said frangible membrane (102) to the housing in the region of said ring-like transformation zone (100).

7. Electrode according to claim 5, wherein said frangible membrane (102) comprises a material sealable to the housing, and secured to the housing in the region of said ring-like transformation zone (100), and break or score lines (103) are formed on the membrane.

8. Electrode according to claim 5, wherein said frangible membrane (102) comprises polypropylene film material.

9. Electrode according to claim 5, wherein said frangible membrane (102) comprises a polypropylene film material and a filler of the material of the group consisting of glass, fiber, mica, talc and mineral filler.

10. Electrode according to claim 1, wherein said terminal means (34) includes silver, and wherein silver chloride is located in at least one of said chamber portions.

11. Electrode according to claim 1, wherein the housing includes a vaulted, dome-shaped structure and the subdividing means comprises a membrane (102) extending across the structure.

12. Electrode according to claim 1, further including rupturing or penetrating projections (138) on the electrically conductive terminal means (34) extending and projecting inwardly in the direction towards said subdividing means (101, 102) to facilitate rupture of the subdividing means upon deformation of said housing consequent to application of pressure thereto.

13. Electrode according to claim 1, further including a laterally extending annular flange (28) extending outwardly from the base of the housing, said protective film extending over said flange, and said pressure sensitive adhesive means (94) being releasably secured over said flange and said membrane, and forming a unitary element,
to permit stripping off of said pressure sensitive adhesive means to adhesively attach the electrode to the surface of the subject with the flange holding the electrode in place, and the microporous membrane (76) being exposed and in contact with the surface of the subject.

14. Electrode according to claim 13, further including breathing openings (110) extending through said flange and said adhesive means (94).

15. A method of transferring electrical current flow between an electrically conductive terminal (34) and a body surface of a subject, said method including
providing a biomedical electrode having
an assembly of
a generally cup-shaped housing (24) of a flexible material including a vaulted, downwardly open dish or cup-like structure, with
an electrically conductive terminal (34) being sealed in and extending through said housing;
a microporous membrane (76) sealed to and extending across said housing at a base thereof,
said membrane closing off said downwardly open structure and defining therein a chamber (66);
subdividing mean (101, 102) subdividing said chamber (66) into a first chamber portion (166, 166a) and a second chamber portion (266, 266a), said subdividing means being of frangible plastic material subject to rupture, the terminal extending into the first chamber portion (166, 166a);
wherein the second chamber portion (266, 266a) is substantially filled by a tissue-compatible electrolyte means (70) the subdividing means (101, 102) separating the electrolyte means (70) and the terminal (34), and
wherein the first chamber portion (166, 166a) retains therein at least one material selected from the group consisting of a surfactant, a skin penetrant, a sweat-inducing agent and an antibacterial agent,
and comprising the steps of
firmly pressing said electrode assembly into positive contact with the body surface and securing said membrane in contact with the body surface;
deforming the walls of said housing to physically transform the shape of the housing to assume a different profile with a resulting change of configuration,
said step of deforming the walls of said housing including rupturing or breaking the subdividing means to release the electrolyte means from said second chamber portion (266, 266a) into said chamber (66) and to establish thereby mechanical contact, and electrically conductive connection between said electrolyte means and the terminal (34), after rupture, and to mix said at least one of the materials in the first chamber portion and the electrolyte means upon rupture or breakage of said subdividing means
and to provide for pressure upon said electrolyte means and urge the electrolyte means through said microporous membrane (76) to establish effective minimal resistance direct electrical contact between the body surface and the terminal.

16. Method according to claim 15, wherein
a surfactant (170) is retained within said first chamber portion (166, 166a).

17. Method according to claim 15, wherein the housing has a vaulted, dome-shaped roof;
and the step of deforming the housing comprises pressing down on the roof of the housing.

18. Methods according to claim 15, wherein the step of deformation of the housing (24) is carried out with sufficient force to cause pressure on the electrolyte means to seek out and penetrate skin pores, hair follicles, and in combination with the substances in the chamber assist the electrolyte means to penetrate sebum, oil and dead skin to achieve optimum electrical conduction with minimal or no prior skin abrasion.

19. Method according to claim 15, wherein the step of deformation of the housing is carried out over an extended time period to induce a continued pressure over the expected period of use, which together with the control over evaporation of the electrolyte means assures more uniform performance over the period of use with much less susceptability to drying out compared to pre-gelled sponge electrodes and thereby assuring more uniformity of signals and less need for replacement.

* * * * *